US005498260A

United States Patent [19]
Rink et al.

[11] Patent Number: 5,498,260
[45] Date of Patent: Mar. 12, 1996

[54] INTERNAL REFLECTANCE ANGLE FIRING FIBER OPTIC LASER DELIVERY DEVICE AND METHOD OF USE

[75] Inventors: John L. Rink, San Francisco; Marilyn M. Chou, Piedmont, both of Calif.

[73] Assignee: Xintec Corporation, Oakland, Calif.

[21] Appl. No.: 67,566

[22] Filed: May 26, 1993

Related U.S. Application Data

[63] Continuation-in-part of Ser. No. 14,814, Feb. 8, 1993.
[51] Int. Cl.[6] .................................................. A61N 5/06
[52] U.S. Cl. .................................. 606/16; 606/15; 606/17
[58] Field of Search ......................... 606/14, 15, 16, 606/17, 6, 7, 2, 3, 10, 11, 12

[56] References Cited

U.S. PATENT DOCUMENTS

| Re. 32,849 | 1/1989 | Wei et al. ........................ 204/192.27 |
| 3,865,113 | 2/1975 | Sharon et al. ..................... 128/303.1 |
| 3,865,114 | 2/1975 | Sharon et al. ..................... 128/303.1 |
| 4,266,547 | 5/1981 | Komiya ............................ 128/303.1 |
| 4,266,548 | 5/1981 | Davi .............................. 128/303.1 |
| 4,266,549 | 5/1981 | Kimura ........................... 128/303.1 |
| 4,309,075 | 1/1982 | Apfel et al. ........................... 350/164 |
| 4,372,642 | 2/1983 | Singer et al. ....................... 350/96.12 |
| 4,458,683 | 7/1984 | Katsuyoshi ........................... 128/395 |
| 4,492,230 | 1/1985 | Sunago et al. ..................... 128/303.1 |
| 4,517,973 | 5/1985 | Sunago et al. ..................... 128/303.1 |
| 4,791,927 | 12/1988 | Menger ........................... 128/303.1 |
| 4,925,259 | 5/1990 | Emmett . |
| 4,940,636 | 7/1990 | Brock et al. ........................... 428/426 |
| 4,950,268 | 8/1990 | Rink ................................... 606/12 |
| 4,992,087 | 2/1991 | Holscher ............................ 65/60.2 |
| 5,000,575 | 3/1991 | Southwell et al. ...................... 356/382 |
| 5,009,920 | 4/1991 | Lee ..................................... 427/9 |
| 5,057,099 | 10/1991 | Rink ................................... 606/12 |
| 5,061,265 | 10/1991 | Abela et al. ............................ 606/15 |
| 5,129,895 | 7/1992 | Vassiliadis et al. ..................... 606/15 |
| 5,143,445 | 9/1992 | Bateman et al. ........................ 362/293 |
| 5,160,668 | 11/1992 | Imus ................................... 264/427 |
| 5,163,935 | 11/1992 | Black et al. ........................... 606/16 |
| 5,242,438 | 9/1993 | Saadatmanesh et al. ................. 606/17 |
| 5,246,436 | 9/1993 | Rowe ................................. 606/16 |
| 5,253,312 | 10/1993 | Payne et al. .......................... 606/15 |
| 5,257,991 | 11/1993 | Fletcher et al. ........................ 606/15 |

FOREIGN PATENT DOCUMENTS

WO91/01687  2/1991  WIPO ........................... A61B 8/12

OTHER PUBLICATIONS

Stein, Barry; "Transurethral Resection of Benign Prostatic Hyperplasia with Advanced Nd: YAG Laser Surgical Systems".
Product Information—BARD©: "Urolase™ Right Angle Laser Fiber"; Part Number 350000.
Product Information—Cytocare: "ProLase II".
Product Information—Laserscope Surgical Systems: "Angled Delivery Device"; Part Number 10–2071.
Product Information—LaserSonics: "UltraLine™ Lateral Firing Quartz Fiber".
Product Information—LaserSonics; "ArthroGuide™ $CO_2$ Laser Fiber Delivery System".

Primary Examiner—Stephen C. Pellegrino
Assistant Examiner—Sonya Harris-Ogugua
Attorney, Agent, or Firm—James J. Leary; Ray K. Shahani

[57] ABSTRACT

The present invention relates generally to a family of fiber optic laser delivery devices for use in medical and other applications, and more particularly, to such an apparatus wherein the transmitted radiation is delivered through and at various angles to the central axis of a fiber optic waveguide by an internally reflective surface. The invention is capable of coagulating, cutting or vaporizing tissue and may be useful in a wide range of surgical and non-surgical applications. A novel method for coagulating and then vaporizing or otherwise removing the coagulated tissue is also disclosed.

28 Claims, 5 Drawing Sheets

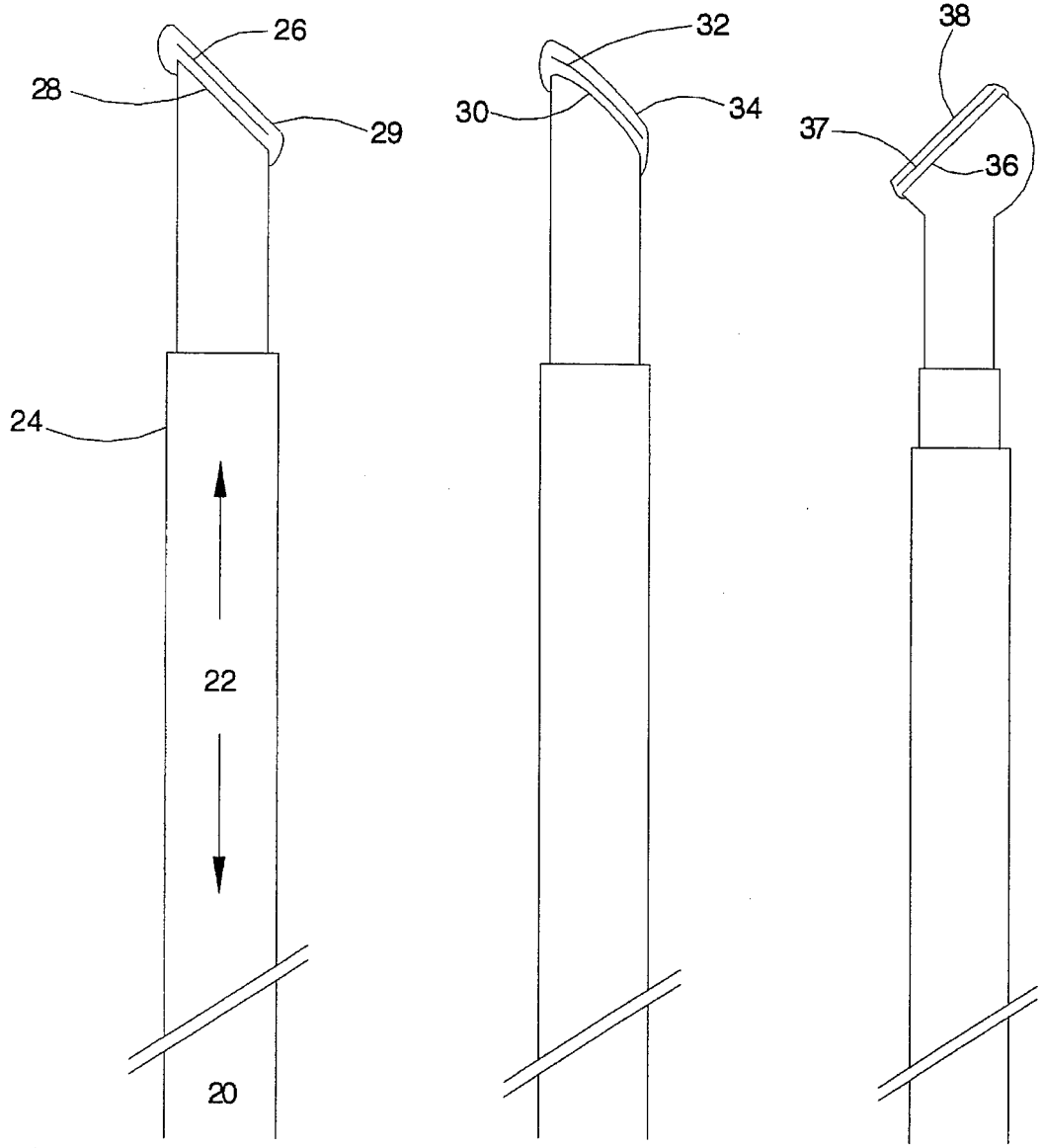

INTERNAL REFLECTANCE ANGLE FIRING FIBER OPTIC LASER DELIVERY DEVICE AND METHOD OF USE

REFERENCE TO RELATED APPLICATION

This is a continuation in part of co-pending patent application Ser. No. 08/014,814 filed Feb. 8, 1993.

FIELD OF THE INVENTION

The present invention relates generally to a family of fiber optic laser delivery devices for use in medical and other applications, and more particularly, to such an apparatus wherein the transmitted radiation is delivered through and at various angles to the central axis of a fiber optic waveguide by an internally reflective surface.

BACKGROUND OF THE INVENTION

Although the first useful lasers were developed in the 1960s, recent advances in laser and fiber optic delivery systems have greatly enhanced the use of this technology in the field of medicine. Today there are numerous types of laser systems designed for operation in a wide range of applications primarily related to surgical and other medical procedures.

A common type of laser known as a CO2 laser delivers radiation with a wavelength of 10.64 microns. However, in order to focus or channel the radiated energy produced by a CO2 laser it is necessary to configure sets of mirrors in certain ways. These systems are typically large and expensive. With the advent of the Nd:YAG type laser delivering electromagnetic energy at a wavelength of 1.064 microns, it became possible to generate and focus the laser radiation through a silica core optical fiber. Thus, fiber optic surgical tools have become important in certain procedures. The range of their utility is still being explored and discovered.

Laser fibers are used in different ways, including incision, necrosis or killing of live tissue, excision or removal of tissue and structure, and cauterization of tissue. During incision and removal of tissue, a beam of laser radiation causes an instantaneous vaporization of the water molecules in the tissue contacted by the beam. The tissue seems to disappear with a puff of steam, leaving behind a very small amount of charred tissue. This process is called ablation, or more specifically photoablation, a term which refers to the removal of live, diseased or dead tissue by vaporization. Incision is accomplished using a very narrow beam directed to a small point drawn across the tissue being incised. A very focused beam would provide the greatest amount of control during either operation.

Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. The process has been likened to frying an egg. In practice, during an incision procedure cauterization of the incised tissue is likely to occur simultaneously. Thus, laser surgery is often characterized by an absence of bleeding during the surgery.

The protocol for a given procedure might specify the type of fiber tip, rate and mode of power delivery, time parameters, etc. Typically, although light at 10.64 is strongly absorbed by the H2O molecule resulting in efficient incision or ablation of soft tissue, a surgeon may be able to defocus the radiation from a CO2 laser and cause a scattering of radiation, with a resulting effect of cauterization. This is the effect of YAG-type laser energy. Since light at 1.064 microns is not strongly absorbed by water molecules the radiant energy scatters or is dissipated throughout the tissue, at and below the surface, and overall coagulation occurs. However, when used in conjunction with a fiber optic surgical tool, the Nd:YAG laser is capable of creating a very narrow beam, thereby making possible incision and ablation as well as cauterization and. coagulation.

In the prior art there are described devices which generate a dual wavelength beam of radiation and are thereby capable of both cutting and cauterizing. Such devices generally use one type of laser with some type of harmonic generator for providing half or double fundamental wavelength beams. There also exist inventions which deliver energy at much shorter wavelengths, such as 250–350 nm. At these wavelengths proteins, as opposed to water molecules, absorb the radiation. These systems, however, are less suitable for general types of surgical operations since they are more complicated to operate. Use of such systems has not become standard in most medical facilities and their cost is generally too high to justify their purchase for occasional use in fairly specialized procedures.

The construction of optical fibers used in surgical procedures is fairly simple. A plastic or silicone cladding is often used to protect the quartz fiber which itself transmits the laser radiation. These types of fibers are termed "multimode" fibers and the beam of photons entering the fiber are all travelling in roughly the same direction. Theoretically, only a few of the entering photons are directed straight down the axis of the fiber. Transmission of the radiant beam is possible since the rest of the photons are constrained to the core of the fiber due to internal reflectance, generally by the outer surface of the fiber or the inner surface of the cladding. Very few photons escape the fiber. The technology related to the use of silica core fibers in medical lasers is well known, e.g. B. P. McCann, Photonics Spectra, May 1990, pp 127–136.

Differences between these types of optical fibers and those used in telecommunications and data transmission are important. Several design factors must be considered such as sterilizability, quartz core integrity and purity, power capacity and index of refraction of materials of construction.

Generally, 20 to 100 watts of energy are used to perform soft tissue surgery. A scalpel used externally might be operated much differently than a scalpel used in internal or endoscopic surgery. Scalpels used with most types of endoscopes are very small. Additionally, often laser surgery is performed with irrigation by a cooling gas or liquid to cool the scalpel firing tip as well as to prevent the tissue from overheating. Some endoscopes have multiple channels to accommodate a viewing port or camera, a laser delivery device, and an irrigation supply and accompanying vacuum channel.

Delivery of high power radiation can have a very damaging effect on the scalpel tip itself. One of the problems with existing designs is that the tip which directs the laser beam to a right angle becomes overheated. This is caused by an absorption of power (heat) at the reflecting surface. Overheating of the firing tip can be caused by an accumulation of incompletely burned tissue which rapidly heats up. Fouling of the firing tip can trigger a process known as thermal runaway. As heat builds up, the firing tip gets hot and sometimes starts to melt or deform. Often, angle firing surgical scalpels will need to be replaced partway through the surgical operation due to this problem.

One solution to firing tip overheating is to provide a transparent, hard, heat resistant tip, such as sapphire or quartz. An alternative is to provide a highly reflective surface in the scalpel tip for deflecting the beam. This invention discloses a device with a reflecting coating deposited or otherwise applied to the transmitting end or firing tip of an optical fiber waveguide such that the beam of radiation is internally reflected out one side of the transmitting end of the waveguide. The invention comprises an internally reflected source of cutting power which could be used in a variety of cutting or heating applications calling for power delivery at an angle to the power source.

One material capable of being deposited in a very thin coating and producing a very high reflectance is gold. A protective layer over the reflective material could also be applied and be useful to add durability and thermal resistance to the reflective material. U.S. Pat. No. 4,992,087, incorporated herein by reference, discloses a reflective coating consisting of a metal or metal alloy and a process for applying it to a glass surface.

Multiple layer optical interference films, also known as interference filters, are well known in the art. Such films comprise alternating layers of two or more materials, typically one with a relatively high index of refraction and the other with a relatively low index of refraction. These materials are also known as dielectrics. Such are well known in the art and can be designed to reflect or transmit light radiation from various portions of the electromagnetic spectrum. Often, materials with high and low indexes of refractivity are applied in alternating layers so as to comprise a "quarter wave stack", each layer having a thickness equal to approximately one quarter wavelength of the incident light wave. These types of reflectors have been described providing optical absorption losses of as little as 0.0001% to 0.0002%.

Methods for manufacturing these films are described in the prior art. U.S. Pat. No. 4,925,259, incorporated herein by reference, describes a damage-resistant dielectric coating formed over a silica substrate. Using a pulsed-plasma assisted chemical vapor deposition process several hundreds and even thousands of layer pairs can be deposited rapidly. Larger differences between the indices of refraction require a lesser number of layer pairs to obtain a given value of reflectance. In some cases, the indices of refractivity of alternating materials can be very similar and the number of layers very great. These coatings seem to have superior damage-resistance to optical radiation, approaching the damage resistance of pure silica. For laser applications using high power, components can be made to withstand high energy flux densities. They are also resistant to abrasion. Since the materials are very similar in composition there are fewer problems associated with differences in thermal and mechanical properties. Peeling and scaling is avoided as are microcracks which, in a given layer, would otherwise occlude the film.

At the reflecting surface, if most of the incident radiation is reflected very little will be absorbed and the temperature at the surface will not rise significantly, especially using today's advanced lasers with pulsed energy, high-peak pulsing and temperature detecting fiber tip protection systems. In the prior art, providing such a reflective coating such as an interference film to internally reflect the beam of a laser used in conjunction with an optical fiber to perform surgical or other cutting or heating procedures is unknown.

Another problem associated with current laser scalpels is that they are often clumsy to use and difficult to manipulate precisely. One problem is that the quartz fiber is so thin it is difficult to grasp effectively, especially if it is used in conjunction with a cystoscope or some type of endoscope where the firing end cannot be controlled directly by the surgeon. Also, as the scalpel is rotated and manipulated by the surgeon, the fiber becomes twisted under a certain amount of angular torque. It would be desirable to provide a scalpel which would be easily controlled, perhaps through the use of some external gripping apparatus attached to the optical waveguide.

Many surgical operations are standard and the procedures followed are routine and well known in the field. For example, in prostate surgery to reduce an enlarged prostate, a typical surgical procedure using a laser scalpel would be to fire energy at four specific anatomic zones causing ablation in very precisely delimited areas in the prostate gland itself. Since the four points procedure is common it would be desirable to provide the surgeon with a scalpel which would select consecutively and precisely the exact points of laser beam contact, making the operation safer and less prone to surgeon error.

The following describes the method for performing a prostatectomy, the removal of tissue from an enlarged prostate gland. Using a laser scalpel, the tissue to be removed is coagulated to kill the tissue, perhaps at the four-points referred to above. Typically this might result in an immediate swelling of the surrounding tissue. Therefore, a catheter would be allowed to remain in place for several days following the operation to allow for drainage of urine. Once the swelling subsides the catheter would be removed and over a period of several weeks the dead tissue would slough off naturally. It would be desirable to provide a scalpel which would allow the surgeon to remove the swollen, coagulated tissue in a subsequent vaporization step during the same operation to avoid the need for the catheter completely. As discussed above, radiation at 1.064 microns is not readily absorbed by water molecules. It appears that the high-peak power output type of laser controller is capable of generating higher temperatures useful for vaporization at the surface.

It would be desirable to have an angle firing scalpel which would not overheat and lose integrity and efficiency. It would also be desirable to have an angle firing scalpel which could both cut tissue and perform the cauterization process, either simultaneously or by the surgeon's control. Such a scalpel should be appropriately sized to be convenient to use. It is believed that the present invention meets these needs.

SUMMARY OF THE INVENTION

It is an object of this invention to provide a more efficient angle firing fiber optic laser scalpel than previously known. This invention is an internal reflectance angle firing fiber optic laser scalpel. The major drawback to devices in the prior art is overheating and failure of the firing tip. This can be attributed to poor structural design of the firing tip. In the present invention the transmitting end of the waveguide is cut and polished at an angle to the central axis of the waveguide. Thus, the precise angle at which the laser beam is directed, whether it be greater than, equal to or less than 90 degrees to the incident beam, can be specified.

Once the tip of the fiber is cleaved at an angle and possibly polished, the reflecting coating would be applied to the end surface. This coating could be of gold or some other metal capable of being deposited or otherwise applied such that nearly 100% of the incident radiation beam would be reflected. Other materials are also currently available which may be transparent at certain wavelengths but which are virtually 100% reflective at a wavelength of 1.064 microns. These materials, or combinations of materials, and the thickness and order in which they would be applied to a surface can be specified by one skilled in the art to provide an interference coating. Such a coating, essentially 100% reflective at 1.064 nm, would be useful with a YAG laser. Furthermore, such coatings could be specified to provide reflectance at virtually any wavelength, allowing the invention to be used with other types of lasers.

Various techniques which currently exist for applying such an internally reflective layer upon a given surface include sputtering, low pressure vapor deposition, corona plasma deposition, and high temperature processing and are well known to those skilled in the art.

It is also within the scope of this invention to provide a protective layer over the reflective coating. In the case of gold and other materials used as a reflecting material, it might be possible to cover the tip with nickel or copper. Other materials are also appropriate. In the case of an interference coating providing reflectance, silicates or other dielectric materials might be appropriate to protect the reflective coating.

With respect to the materials of construction of both metal coatings as well as interference coatings and their respective protective layers, design factors which might be important include thermal stability, compatibility of coefficients of thermal expansion, bond strength, lack of adverse optical interaction with the reflected beam, durability, etc.

It is also important to prevent the protective layer from being applied to certain parts of the fiber, for example the end of the fiber through which the reflected beam is transmitted. Any material applied to the end of the optical fiber in this region could have the effect of absorbing a small amount of the incident radiation and causing an increase in the temperature of the firing tip. It could also have the effect of producing some other less uniform reflectance pattern.

It is a further object of this invention to provide the medical practitioner with an instrument which can be manipulated efficiently and precisely. The device can be used alone or in conjunction with a fiber gripping and positioning apparatus. It could also be assembled with a cannula section surrounding the fiber to protect the fiber and allow manipulation of the transmitting end of the fiber.

This invention can be used for external surgery or internal surgery, for example through the internal lumen of a cystoscope or other type of endoscope. As mentioned, the scalpel can be operated precisely using a positioning device. This device would be assembled with the optical fiber and would allow the scalpel to be accurately retracted or extended into the region being operated upon. The positioning device can feature a side position indexing mechanism which could be useful in standard operations, for example, in prostate surgery as discussed above, using a channel of a cystoscope or other lumen. This type of device would allow the surgeon to select and maintain the depth to which the scalpel is inserted. Then the device could be manipulated by the operator to direct the transmitted radiation to any given position or to specific predetermined positions.

It is also an object of this invention to provide an internally reflected fiber optic laser scalpel with a beam which converges in a region near the tip of the fiber and thereafter diverges. By giving the transmitting end of the fiber a rounded, spherical shape, the reflective surface applied thereon becomes concave and will reflect the laser beam into a somewhat cone shaped converging beam which narrows through a short region and thereafter becomes a cone shaped diverging beam. The hottest point in the beam pattern would be in this narrow region. A curvature could be chosen to provide a single instrument capable of performing the coagulation function in the broader regions of the beam pattern and vaporization of tissue in the hottest region of the radiated beam.

A novel method for removing tissue is disclosed. The method entails the use of a laser source with a power output regulator and can provide a pulsed, high-peak power output. The tissue is first coagulated and then removed using a higher power output.

BRIEF DESCRIPTION OF THE DRAWINGS

FIG. 2 is a cross section view of the firing tip of one preferred embodiment of the invention.

FIG. 3 is a cross section view of the firing tip of another preferred embodiment of the invention.

FIG. 4 is a cross section view of the firing tip of another preferred embodiment of the invention.

DETAILED DESCRIPTION OF THE INVENTION

Figure 1A:
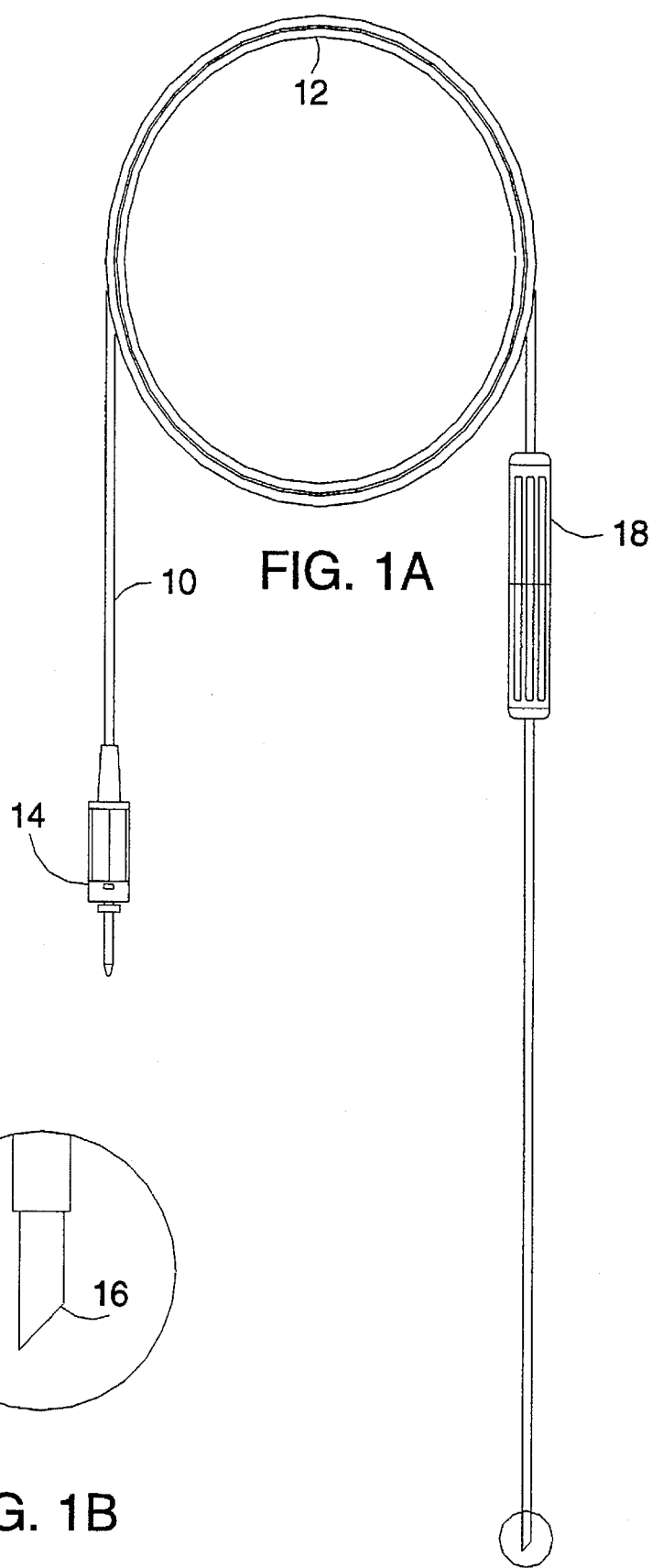
FIG. 1A is a schematic illustration of the present invention with a depth positioning device attached.

FIG. 1A is a view of the present invention, a surgical scalpel. At the receiving end 10 of the optical fiber waveguide 12 there is a releasable optical fiber connector 14. These connectors are standard in the industry and can also be proprietary. The fiber has a firing tip 16.

Also shown is a positioning apparatus 18 for use when the scalpel is operated with a lumen or endoscope or in some other type of procedure. The distance through which the scalpel is inserted into a rigid cannula or channel of an endoscope can be adjusted and precisely positioned by the surgeon during a surgical operation. The apparatus can be precisely positioned on the flexible fiber and will be convenient to use without hampering the operation of the scalpel, meanwhile aiding the surgeon. It can be considered as a handle or gripping system for the fiber. One such apparatus would be made of two sections which screw together. As the two parts screw together they would clamp or pinch onto the fiber itself. Thus, the positioning apparatus would be slidably attached to the fiber and would give a further degree of control to the operator. The device could also have a adjustment means for metering a precise length of fiber through the positioning apparatus or for metering rotation about the central axis of the device.

Figure 1B:
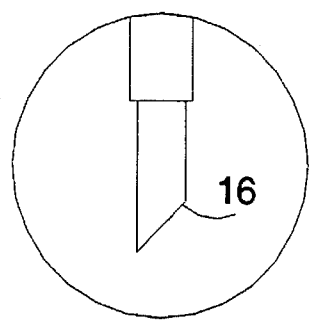
FIG. 1B is an enlargement of the angle firing tip.

FIG. 1B is an enlarged view of the firing tip 16 of FIG 1A.

FIG. 2 is a cross section view of a preferred embodiment of the firing tip of the scalpel. As shown, the fiber 20 is cleaved at an angle, other than perpendicular, to the central axis 22 of the fiber. The cladding of the fiber 24 is removed near the firing tip.

The reflective coating 26 is only applied to the fiber end surface 28 exposed at the cleaved end of the fiber. The reflective layer may be some sort of interference coating comprised of several layers of materials with alternating high and low indexes of refraction. By varying the materials, thicknesses, and number of layers applied, very specific shape and directional patterns of reflectance can be produced by such coatings. With some materials, such as gold or other metals or materials, a minimum thickness is required.

Also in FIG. 2 is a protective layer 29 over the reflective coating. This layer would be durable and bond efficiently to the reflective layer. This coating can be applied by sputtering, vapor deposition or in other ways known to those skilled in the art. For example, if the protective coating is a type of glass or ceramic the coating could be applied in a molten state or could be produced using some other high temperature process.

FIG. 3 is a cross section view of another preferred embodiment of the firing tip. In this embodiment the cleaved end of the optical fiber has a curvature providing a rounded surface 30 to apply the reflective coating 32. This curvature provides a reflective surface which will focus the beam through a narrow region. When the radiant energy beam impinges on the somewhat concave reflective surface the beam is reflected and forms an elliptical cone shaped beam, narrowing through a focal region outside of and beyond the end of the fiber, and thereafter widening. By increasing the radius of curvature of the reflecting surface, the focal point of the incident beam can be extended to points farther away from the firing window of the firing tip. Also shown is a protective layer 34 applied over the reflective coating. With this invention it is possible to provide the surgeon with a range of focal length tools which can coagulate as well as ablate tissue.

FIG. 4 is a cross section view of another preferred embodiment of the firing tip. In this embodiment the diameter of the optical fiber waveguide increases near the firing tip. One way to make this tip would be to heat the end of a silica fiber. As the tip melts the molten silica will coalesce at the end and form a bead or drop of molten silica. Alternatively, the tip of a fiber could be fused to the end of a section of silica rod having a greater diameter than that of the fiber itself. Then, the bead or enlarged extension can be given a bias cut and polished. The resulting tip will have an elliptical end surface which is larger than that produced by a cleaved fiber alone. Therefore, the laser beam produced upon reflection will have a greater cross sectional area also. Thus, laser energy will be transmitted through the fiber onto the enlarged end surface 36. A metal coating or an optical interference coating 37 and, if desired, the protective layer 38, can then be applied. This embodiment could be useful when a relatively broader beam is required but a non-diverging beam is desirable. Additionally, the end could be formed like that in FIG. 3 so as to provide a diverging beam.

Figure 5A:
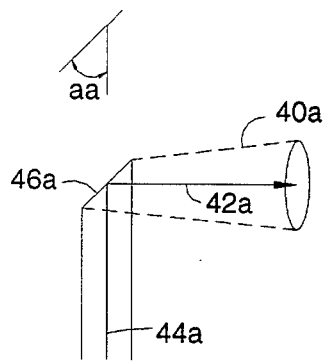
FIGS. 5A, 5B and 5C show varying angles of reflection.
Figure 5B:
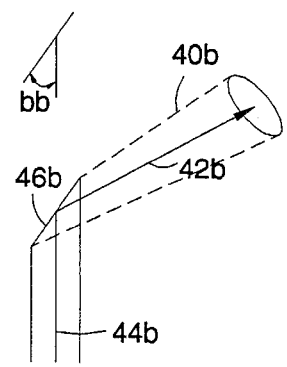
Figure 5C:
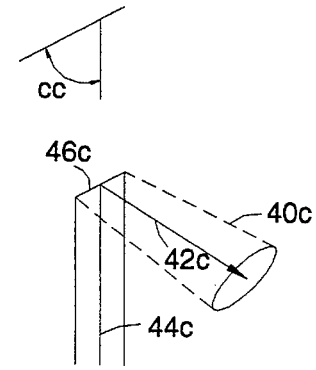

FIGS. 5A, 5B and 5C show how the angle of reflectance of the laser beam can be varied according to the angles at which the reflective surface is positioned. The illustrations show the reflected beam patterns 40a, 40b, 40c after reflectance as elliptical and widening. The central axes of these patterns 42a, 42b and 42c are shown as approximately equal to, greater than and less than 90 degrees with respect to the central axes of the optical fibers 44a, 44b and 44c. There is a minimum angle which must not be exceeded, beyond which the reflected energy would have a destructive effect upon the firing end itself.

The bias cut end surfaces 46a, 46b and 46c of the fiber tips shown in FIGS. 5A, 5B and 5C lie at an angle with respect to the central axes of the optical fibers 44a, 44b and 44c. This angle is shown as aa, bb and cc, respectively. This angle is approximately equal to 45 degrees when the laser beam angle of reflectance is approximately 90 degrees, as shown by aa. If the end surface of the bias cut fiber is placed at an angle less than 45 degrees off from the central axis, as shown in bb, the angle of reflectance is greater than 90 degrees. Similarly, if the end surface of the bias cut fiber is placed at an angle greater than 45 degrees off from the central axis, as shown in cc, the angle of reflectance will be less than 90 degrees.

Figure 6A:
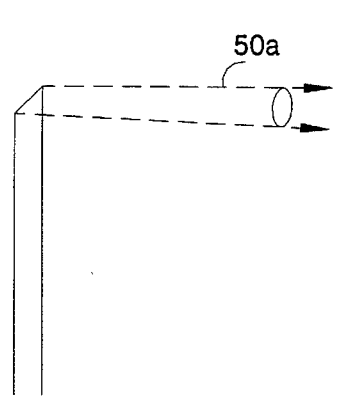
FIGS. 6A and 6B show two different beam paths generated by two different embodiments of the firing tip.
Figure 6B:
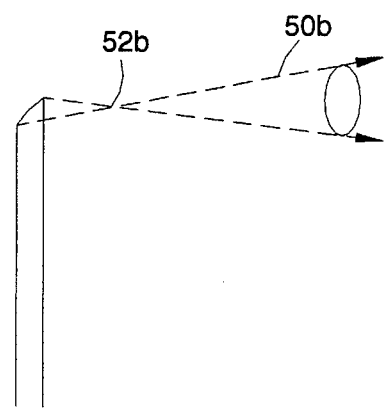

FIGS. 6A and 6B are schematic illustrations of the reflected beam patterns which would be produced by firing tips shown in the two embodiments in FIGS. 2 and 3. In both embodiments the incident beam impinges upon the reflective surface. In FIG. 6A the reflected beam pattern 50a is nearly as large in diameter as the incident beam at a point near the reflective surface but which is slightly divergent thereafter. This embodiment could be used in a surgical application where tissue cutting or ablation is desired, as the intensity of the beam is fairly uniform throughout its length and is relatively narrowly focused In FIG. 6B the reflected beam 50b is cone shaped, narrowing or converging through a region 52 corresponding with the focal point of the curved reflective surface, and thereafter widening. The cross section area of the beam pattern near 52 is very small. Thus, cutting or tissue ablation is possible when the scalpel of FIG. 3 is positioned so that the laser beam impinges upon the tissue at a point near the focal region of the radiant beam. However, this embodiment may also be effective for coagulating tissue if the scalpel is positioned in such a way as to allow the reflected beam to impinge upon the tissue at a point somewhat between the reflective surface and the focal region or, alternatively, at a point somewhat beyond the focal region. Thus, this embodiment of the invention can be used for coagulation of tissue as well as for tissue removal or incision.

Figure 7A:
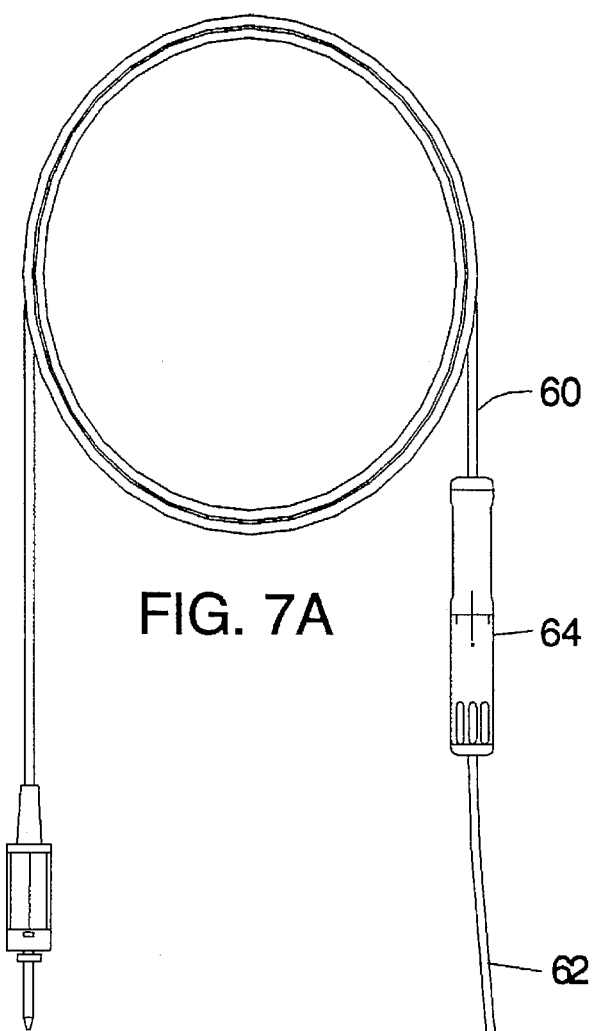
FIG. 7A is a view of one preferred embodiment of the invention assembled with a rigid or semi-rigid cannula and having an indexed side positioning device.
Figure 7B:
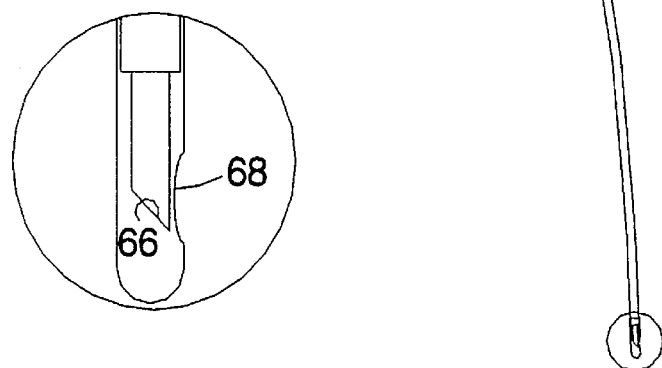
FIG. 7B is an enlargement of the angle firing tip.

In FIG. 7A another preferred embodiment of the invention is shown. Here, the optical fiber waveguide 60 would slide into a rigid cannula member 62 with a rotatable indexed locking device 64 mounted at the end opposite the firing tip, which would lock onto the fiber cladding. Such a locking device could be indexed so as to twist and lock into fixed positions axially. The cannula member could even be semi-flexible in that it could bend a certain amount but rigid with respect to maintaining it's hollow, tubular shape. The firing tip shown enlarged in FIG. 7B is disposed within the distal end of the cannula member. The fiber is adjusted such that the reflective surface 66 on the firing tip directs the reflected beam out the firing window 68. The tip can be shaped as is shown in FIGS. 2, 3 or 4. The cannula member could be made detachably attached to the indexed position locking device. This embodiment of the invention is useful for operations using a cystoscope or other endoscope. The entire cannula member turns with the internal fiber. The positioning means, similar to that of the embodiment of FIG. 1, would allow the fiber to be inserted into the cannula member and tightened into place. Then, the cannula member would rotate with the fiber itself in order to direct the firing window on the cannula member toward the intended region.

The embodiments of this invention can be used for various operations, including coagulating, incising or removing tissue. The invention can be used with an endoscope with or without a separate lumen for the scalpel itself. The tissue to be removed can first be coagulated and then vaporized.

As disclosed in U.S. Pat. No. 4,950,268, incorporated herein by reference, a laser driver and control circuit can be obtained which will produce a pulsed, high-peak power laser. Using such a laser source, a scalpel can be used to coagulate tissue using a power output of approximately 30–50 watts. Then, the power output of the laser can be increased to approximately 60–80 watts and the coagulated tissue can be vaporized. It may be advantageous to reduce the flow of cooling fluid around the firing tip during the vaporization step of the operation because the cooling fluid would also have the effect of cooling the affected tissue and preventing vaporization. The exact parameters of the operation must be chosen by the surgeon who has ultimate control over power output, scalpel design, degree of cooling fluid flow, etc.

Figure 8A:
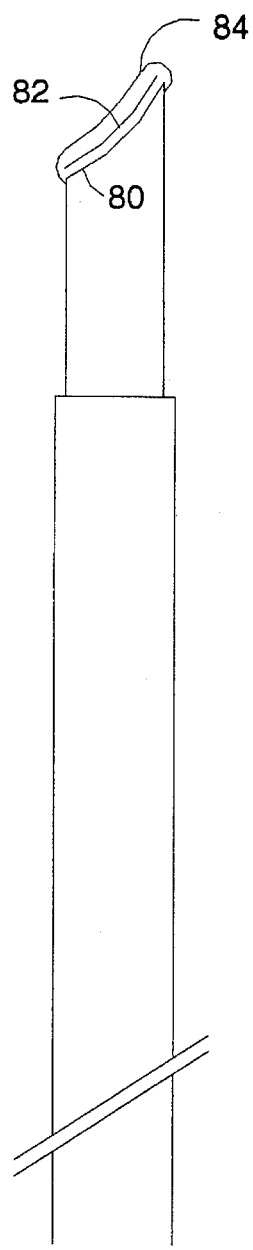
FIG. 8A is a cross section view of the firing tip of another preferred embodiment of the invention.

FIG. 8A is a cross section view of the firing tip of another preferred embodiment of the invention. This embodiment is similar to that shown in FIG. 3. However, rather than having a convex transmitting end, the optical fiber firing tip 80 has been given a concave shape, i.e., the firing tip is shaped like the inside surface of a sphere. The reflective coating 82 now has a convex shape, similar to that of the outside surface of a sphere. In this embodiment the protective layer 84 is also somewhat convex, as indicated.

Figure 8B:
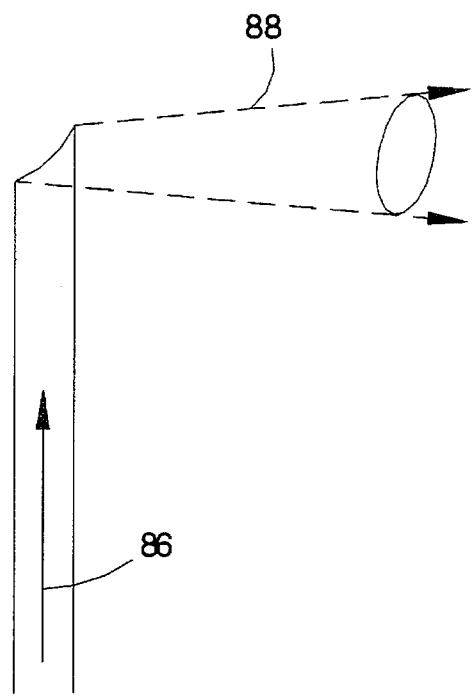
FIG. 8B is a beam path generated by the firing tip of the embodiment of FIG. 8A.

FIG. 8B is a beam path generated by the fixing tip of the embodiment of FIG. 8A. As shown, transmitted energy traveling in the direction indicated by 86 will impinge upon the convex reflective coating and will be reflected into an elliptical cone shaped beam 88, widening after reflection. In this embodiment, it is important to note that, as opposed to the embodiment of FIG. 3, the reflected beam will not converge through a point in front of the firing tip before diverging. No focal point is created by the reflected beam since the convex reflective coating will not focus the reflected beam. This embodiment will tend to be useful wherever a broad, coagulating beam is desired. As discussed previously, a sharp defined point of laser radiation will be effective for vaporizing tissue at that spot close to the surface of tissue being treated, whereas a broader, more diffuse beam of radiation will tend to coagulate tissue in a deeper region of the tissue.

We claim:

1. An internal reflectance angle firing fiber optic laser scalpel, said scalpel comprising a fiber optic waveguide having:
   a receiving end;
   a central axis; and
   a firing tip, said firing tip comprising:
      an end surface, said end surface lying at an operative angle to said central axis of said waveguide, said end surface of said optical fiber having a concave shape; and
      a reflective coating applied to said end surface such that the reflective coating provides a convex reflective surface.

2. The invention of claim 1 wherein said end surface lies at an angle of approximately 45 degrees with respect to said central axis.

3. The invention of claim 1 wherein said end surface lies at an angle greater than 45 degrees with respect to said central axis.

4. The invention of claim 1 wherein said end surface lies at an angle less than 45 degrees with respect to said central axis.

5. The invention of claim 1 wherein said reflective coating consists of a dielectric material.

6. The invention of claim 1 wherein said reflective coating consists of a metallic material.

7. The invention of claim 1 wherein said reflective coating consists of a plurality of layers of material, said materials having different indices of refraction.

8. The invention of claim 1 wherein said firing tip further comprise a protective layer applied over said reflective coating.

9. The invention of claim 1 wherein said fiber optic waveguide is enlarged near said firing tip providing said end surface with an increased area.

10. The invention of claim 1 wherein said receiving end of said waveguide further comprises a means for coupling said waveguide to a source of radiant energy.

11. The invention of claim 1 further comprising a positioning device, said positioning device having a locking means for attaching said positioning device to said waveguide at a point intermediate said receiving end and said firing tip end of said waveguide.

12. The invention of claim 11 wherein said positioning device further comprises a rotatable section, said rotatable section being disposed between said locking means of said positioning device and said receiving end of said waveguide, said rotatable section being rotatable about said waveguide's central axis.

13. The invention of claim 12 wherein said rotatable section is indexed so as to provide rotation into a plurality of predetermined positions.

14. The invention of claim 11 wherein said positioning device further comprises an elongated tubular cannula member, said cannula member having a proximal end and a distal end, said distal end having a firing window in said cannula member such that said end surface end of said waveguide is positioned in an operative position adjacent to said firing window within said cannula member.

15. An internal reflectance angle firing fiber optic laser scalpel, said scalpel comprising a fiber optic waveguide having:
   a receiving end;
   a central axis; and
   a firing tip, said firing tip comprising:
      an end surface, said end surface lying at an operative angle to said central axis of said waveguide, said end surface of said optical fiber having a convex shape; and
      a reflective coating applied to said end surface such that the reflective coating provides a concave reflective surface.

16. The invention of claim 15 wherein said end surface lies at an angle of approximately 45 degrees with respect to said central axis.

17. The invention of claim 15 wherein said end surface lies at an angle greater than degrees with respect to said central axis.

18. The invention of claim 15 wherein said end surface lies at an angle less than 45 degrees with respect to said central axis.

19. The invention of claim 15 wherein said reflective coating consists of a dielectric material.

20. The invention of claim 15 wherein said reflective coating consists of a metallic material.

21. The invention of claim 15 wherein said reflective coating consists of a plurality of layers of material, said materials having different indices of refraction.

22. The invention of claim 15 wherein said firing tip further comprises a protective layer applied over said reflective coating.

23. The invention of claim 15 wherein said fiber optic waveguide is enlarged near said faring tip providing said end surface with an increased area.

24. The invention of claim 15 wherein said receiving end of said waveguide further comprises a means for coupling said waveguide to a source of radiant energy.

25. The invention of claim 15 further comprising a positioning device, said positioning device having a locking means for attaching said positioning device to said waveguide at a point intermediate said receiving end and said firing tip of said waveguide.

26. The invention of claim 25 wherein said positioning device further comprises an elongated tubular cannula member, said cannula member having a proximal end and a distal end, said distal end having a firing window in said cannula member such that said transmitting end of said waveguide is positioned in an operative position adjacent to said firing window within said cannula member.

27. The invention of claim 25 wherein said positioning device further comprises a rotatable section, said rotatable section being disposed between said locking means of said positioning device and said receiving end of said waveguide, said rotatable section being rotatable about said waveguide's central axis.

28. The invention of claim 27 wherein said rotatable section is indexed so as to provide rotation into a plurality of predetermined positions.

* * * * *